United States Patent [19]

Lifshitz et al.

[11] Patent Number: 5,525,472
[45] Date of Patent: Jun. 11, 1996

[54] METHOD FOR PRODUCTION AND PURIFICATION OF RECOMBINANT APOLIPOPROTEIN E FROM BACTERIA

[75] Inventors: Ruth Lifshitz; Meir Fischer; Benjamin Greenman, all of Rehovot, Israel; Daniel Bartfeld, Ontario, Canada

[73] Assignee: Bio-Technology General Corp., Iselin, N.J.

[21] Appl. No.: 333,872

[22] Filed: Nov. 3, 1994

Related U.S. Application Data

[63] Continuation of Ser. No. 59,889, May 10, 1993, abandoned, which is a continuation of Ser. No. 721,159, Jun. 26, 1991, abandoned.

[51] Int. Cl.$^6$ .............................. C12N 1/38; C12P 21/00; C07K 1/30; C07K 14/775
[52] U.S. Cl. ..................... 435/69.6; 435/244; 435/803; 935/38; 530/359; 530/380; 530/420; 530/422
[58] Field of Search ..................................... 435/69.6, 244, 435/803; 935/38; 530/359, 380, 420, 422

[56] References Cited

U.S. PATENT DOCUMENTS

| | | | |
|---|---|---|---|
| 4,943,527 | 7/1990 | Protter et al. | 435/69.6 |
| 5,049,488 | 9/1991 | Baer et al. | 435/172.3 |
| 5,089,602 | 2/1992 | Isliker et al. | 530/359 |
| 5,116,739 | 5/1992 | Teranishi et al. | 435/69.6 |

FOREIGN PATENT DOCUMENTS 0156355  10/1985  European Pat. Off. .

OTHER PUBLICATIONS

Weisgraber et al., *J. Biol. Chem.* 256:9077–9083, (Sep. 1981).
MacDonald et al., *App. Envir. Microbiol.* 56:640–645 (Mar. 1990).
Vogel et al., *J. Cell. Biochem.*, Suppl. 11C:62 (1987).
de Jong et al., *Bioc. & Biop. Res. Comm.* 119:657–662 (Mar. 1984).
Ribeiro et al., *Bioc. & Biop. ACTA* 1087:219–225 (1990).
Rawn, *Biochemistry*, pp. 209, 210, and 457 (1989).
Atkinson et al., *Biochem. Eng. & Biotech. Handbook*, pp. 54–55 (1983).
Gibson et al., *Clin. Chem.* 30(11): 1784–1788 (1984).
*DIFCO Manual*, pp. 60–61 (1984).
Powell et al., *J. Gen. Appl. Microbiol* 27: 185–194 (1981).

*Primary Examiner*—Stephen G. Walsh
*Attorney, Agent, or Firm*—John P. White

[57] ABSTRACT

Applicants describe methods for purifying human ApoE or analog thereof from recombinant bacterial cells with minimal protein aggregation and degradation during the purification process. The invention involves the addition of neutralized fatty acids to the medium during cell disruption and the use of a non-ionic detergent during the purification process. Additionally applicants describe a method for increasing the production of ApoE or analog thereof in a bacterial host by adding to the culture medium neutralized fatty acids, fatty acid precursors, triglycerides, triglyceride precursors or acetate. Pharmaceutical and diagnostic uses of the ApoE analog are described.

6 Claims, 4 Drawing Sheets

METHOD FOR PRODUCTION AND PURIFICATION OF RECOMBINANT APOLIPOPROTEIN E FROM BACTERIA

This application is a continuation of U.S. Ser. No. 08/059,889, filed May 10, 1993, which is a continuation of U.S. Ser. No. 07/721,159, filed Jun. 26, 1991, both now abandoned.

BACKGROUND OF THE INVENTION

Apolipoprotein E (ApoE) is a protein found in the bloodstream in association with a variety of cholesterol and lipid-containing particles. The role of ApoE in metabolism has been reviewed by R. W. Mahley *Science*, 240: 622–630 (1988), and the complete amino acid sequence of human ApoE has been determined by Rall et al., *J. Biol. Chem.* 257(8): 4171–4178 (1982).

Through its ability to mediate lipoprotein binding and uptake by lipoprotein receptors, i.e. the LDL receptor and the chylomicron receptor, plasmatic ApoE (p-ApoE) has important functions in the regulation of plasma lipoprotein metabolism and in the maintenance of cholesterol homeostasis. Extensive epidemiological studies have strongly indicated a correlation of high blood-cholesterol levels to heart attacks and strokes, due to the formation of atherosclerotic plaques, the production of which is influenced by both genetic and environmental factors (M. S. Brown and J. L. Goldstein, *Science* 232: 34 (1986)). Administration of exogenous ApoE may assist in the regulation of serum lipid and cholesterol levels, and in the prevention of atherosclerosis.

In addition, ApoE is produced at a high level and accumulates in the region of injured and regenerating peripheral nerves (M. J. Ignatius et al., *Proc. Natl. Acad. Sci.* U.S.A. 83: 1125 (1986); G. J. Snipes et al., *Proc. Natl. Acad. Sci.* U.S.A. 83: 1130; P. A. Dawson et al., *J. Biol. Chem.* 261: 5681 (1986)). ApoE may be involved in the mobilization and possible reutilization of lipid or the repair, growth and maintenance of myelin and axonal membranes (T. Vogel et al. *Proc. Natl. Acad. Sci.* U.S.A. 82: 8696 (1985)).

Apolipoproteins including ApoE have also been shown to have immunoregulatory activity (R. W. Mahley et al., *J. Lipid Res.* 25: 1277 (1984); R. W. Mahley & T. L. Innerarity, *Biochem. Biophys. Acta* 737, 197 (1983)). ApoE-containing lipoproteins as well as low density lipoproteins have the capacity to inhibit or stimulate antigen-induced and mitogen-induced T lymphocyte activation and proliferation (R. W. Mahley, *Science* 240: 622–630 (1988)).

However, it is impossible to obtain from human blood sufficient quantities of naturally-occurring ApoE to examine the beneficial therapeutic effects which may be associated with ApoE. Accordingly, there is a need to provide a practical means of producing sufficient quantities of highly purified ApoE to conduct animal and clinical trials and for widespread pharmaceutical use.

The subject invention provides a novel purification method for producing large quantities of highly purified, biologically active, recombinant apolipoprotein E (r-ApoE). This method involves several novel features to solve inter alia problems connected with (1) aggregation and degradation of ApoE, (2) separation of active and inactive forms of ApoE, and (3) removal of endotoxins.

European Patent Publication EP 205,715 assigned to Mitsubishi Chemical Industries Ltd. disclosed the cloning of ApoE in *E. coli* yeast and CHO cells. However, the disclosure indicated that only minute amounts of ApoE were produced and did not include a purification method.

PCT Publication WO 87 02061 assigned to Biotechnology Research Partners Ltd. disclosed the expression of fusion proteins containing the receptor recognition domain of ApoE for drug delivery. This publication does not disclose a method for production or purification of the full length ApoE analog protein.

PCT Publication WO 87 02059 also assigned to Biotechnology Research Partners Ltd. disclosed the correlation of polymorphisms in apolipoproteins (including ApoE) with atherosclerosis, but not a method for production or purification of ApoE.

Japanese Patent Application No. JP 61096998 assigned to Mitsubishi Chemical Industries Ltd. described the cloning and expression of apolipoprotein A-1 analog.

Japanese Patent Application No. JP 60163824 assigned to Nippon Shinyaku KK described the use of serum lipoproteins including ApoE as drug carriers for intravenous injection. The ApoE in JP 60163824 is not derived from recombinant sources.

Co-assigned, copending patent applications U.S. Ser. No. 896,750, filed on Aug. 14, 1986 and U.S. Ser. No. 085,651, filed on Aug. 14, 1987 (a CIP of U.S. Ser. No. 896,750) disclosed methods directed to small scale purification of ApoE. While the recombinant ApoE analogs produced by these methods were very pure, it was necessary to develop a suitable method for industrial production scale-up. Further, it was desirable to produce an ApoE analog containing lower endotoxin levels than those previously produced. Specifically, the method disclosed in U.S. Ser. No. 896,750 produces an ApoE analog which is greater than 90% pure but has an endotoxin level in the range of 500,000–1,000,000 pg/mg.

The method described in U.S. Ser. No. 085,651 utilizes a urea solution throughout and involves batch chromatography on Phenyl-SEPHAROSE™, Heparin-SEPHAROSE™ and DEAE-SEPHAROSE™ (SEPHAROSE™ is a trademark for a specific cross-linked agarose matrix) columns. The resulting ApoE analog is greater than 95% pure and contains less than 2,000 pg endotoxin per mg. The use of urea necessitated the performance of the chromatography steps at 4° C.–10° C. because urea is unstable and the ApoE analog tends to degrade and aggregate in the presence of urea unless the experiments are performed in low temperatures.

Additionally, the chromatography methods in U.S. Ser. No. 085,651 are batch methods involving overnight stirring, conditions which make scale-up very difficult. The endotoxin level of the resulting analog is still high.

The novel methods described herein, i.e. Scheme I and Scheme II, use Triton X-100 (Triton$^R$) to protect ApoE from degradation and aggregation. Triton$^R$ allows the ultrafiltration and column chromatography step to be performed at room temperature. In addition, no batch steps are required in this process. The methods are therefore suitable for scale-up.

Furthermore, Triton$^R$ enables the use of acidic pH conditions; this is a distinct advantage since acidic pH conditions in the absence of Triton$^R$ lead to precipitation of the ApoE analog. The addition of Triton$^R$ allows the enrichment of ApoE by an acidic pH extraction step and also the use of cation exchange chromatography.

The ApoE analog produced by the methods disclosed herein is extremely pure and has a very low endotoxin level, i.e. about 25 pg/mg; therefore, the resulting ApoE analog can be used for animal trials. We have shown that the resulting ApoE analog can be lyophilized and still retains its biological activity on subsequent dissolution, and we have demonstrated that the lyophilized ApoE is very stable.

BRIEF DESCRIPTION OF THE FIGURES

FIGS. 1A and 1B represent two different r-ApoE preparations, batches 01 and 02 respectively. These batches were produced from two different fermentations and were purified as described in Example 3. FIG. 1C represents a p-ApoE preparation and FIG. 1D represents a buffer control. The retention time for both batches of r-ApoE and for p-ApoE were 41.0, 41.37, and 41.40 minutes, respectively both prepared as described in Example 3. The MW of both r-ApoE and p-ApoE were estimated, from a MW standard calibration curve comprising 67 KD (BSA), 32 KD (superoxide dismutase) and 21 KD (human growth hormone), to be approximately 65 KD indicating a dimer form. The additional peak of high MW (about 5%) which appears in batch 01 (FIG. 1A) may represent a slight aggregation in this preparation.

The UV spectra of r-ApoE batch 01 (A) and batch 02 (B) were compared to p-ApoE. UV absorbance was measured in the range of 350–200 nm, and the spectra were found to be identical.

Plasmid pTVR 590-4, which thermoinducibly expresses met-ApoE analog, is shown in this figure and is described in Example 1.

FIG. 4: Comparison of Recombinant ApoE and Plasmatic ApoE by SDS—Polyacrylamide Gel Electrophoresis Samples from each preparation were applied on to a 12.5% polyacrylamide-SDS gel. Lanes A and A' denote r-ApoE (Batch 01); lanes B and B' denote r-ApoE (Batch 02); lanes C and C' denote p- ApoE. All lanes except for C' were loaded with approximately 25 µg, while C' was loaded with 6 µg. Lanes A, B and C were prepared with buffer containing 2-mercaptoethanol (2 ME); lanes A', B' and C' were prepared without 2 ME. After electrophoresis the gel was stained with Coomassie blue reagent. The main bands for r-ApoE and p-ApoE migrate in a similar fashion. The low molecular weight (MW) band of r-ApoE (A, B) which appears just below the main band represents a cleavage product. The upper MW band that appears in lanes A', B', and C' (material applied without 2 ME) may represent sulfhydryl bonded multimers of ApoE. The p-ApoE (C) shows an additional band slightly above the main band which represents the glycosylated form of the plasmatic protein.

SUMMARY OF THE INVENTION

The present invention provides methods for purifying ApoE or analog thereof from a bacterial cell with minimal protein aggregation and degradation during the purification process. The preferred embodiment of the invention provides for a method of extracting ApoE or analog thereof from the cell pellet which comprises: (a) culturing bacterial cells which produce ApoE or analog; (b) disrupting the cell wall of the bacterial cell in a buffer containing magnesium ions to produce a lysate; (c) separating cellular debris and insoluble precipitate from the lysate to obtain a pellet containing ApoE or analog; (d) solubilizing the separated pellet containing ApoE or analog with a solution containing a non-ionic detergent to obtain solubilized ApoE or analog; (e) treating the solubilized ApoE or analog so as to concentrate and purify the ApoE or analog in the presence of a non-ionic detergent; and (f) recovering the resulting concentrated, purified ApoE or analog thereof.

The present invention also provides a method for purifying ApoE or an analog thereof from bacterial cell extract supernatant. Additionally the present invention provides for a method for increasing the production of ApoE or analog thereof in a bacterial host by adding to the culture medium neutralized fatty acids, fatty acid precursors, triglycerides, triglyceride precursors or acetate.

DETAILED DESCRIPTION OF THE INVENTION

The present invention provides methods for obtaining a purified recombinant ApoE or polypspride analog thereof from genetically engineered bacterial cells which produce the recombinant ApoE or polypspride analog thereof. The preferred embodiment of the invention provides for a method of obtaining a purified recombinant ApoE or polypeptide analog thereof from genetically engineered bacterial cells which produce the recombinant ApoE or polypeptide analog thereof which comprises: (a) culturing the genetically engineered bacterial cells so as to produce the recombinant ApoE or polypeptide analog thereof; (b) treating the bacterial cells in the presence of magnesium ions so as to obtain a lysate containing insoluble recombinant ApoE or polypeptide analog thereof; (c) recovering from the lysate insoluble material including insoluble recombinant ApoE or polypeptide analog thereof; (d) treating the insoluble material so recovered with a solution containing a non-ionic detergent to obtain solubilized recombinant ApoE or polypeptide analog thereof; (e) treating the solubilized recombinant ApoE or polypeptide analog thereof so as to concentrate and purify the recombinant ApoE or polypeptide analog thereof; and (f) recovering the resultant concentrated purified recombinant ApoE or polypeptide analog thereof.

The invention is further exemplified as described below.

1. Bacterial Cells Producing ApoE Analog

As used herein, an analog of ApoE is defined as a polypeptide having an amino acid sequence substantially identical to that of naturally occurring ApoE but differing from it by the addition, deletion or substitution of one or more amino acids while retaining the biological activity of naturally occurring ApoE.

The bacterial cell can be any bacterium in which a DNA sequence encoding apolipoprotein E or an analog thereof has been introduced by recombinant DNA techniques. The bacteria must be capable of expressing the DNA sequence and producing the protein product.

The bacteria can be any strain including auxotrophic, prototrophic and lytic strains, $F^+$ and $F^-$ strains, strains harboring the $cI^{857}$ repressor sequence of the lambda prophage and strains wherein the deo repressors or the deo gene have been deleted.

Examples of wild type E. coli strains are prototroph ATCC No. 12435 and auxotroph MC1061 (ATCC No. 67361).

Examples of *E. coli* strains which harbor the lambda cI$^{857}$ repressor sequence are the auxotrophs A1645 containing plasmid pTVR 279-8 (ATCC No. 53216), A1637 containing plasmid pTV104(2) (ATCC No. 39384) and A2097 containing plasmid pSODα2 (ATCC No. 39786); and the prototrophs A4200 containing plasmid pHG44 (ATCC No. 53218) and biotin-independent A4346-containing plasmid pHG44 (ATCC No. 53218).

An example of a lytic *E. Coli* strain is A4048 containing plasmid pHG44 (ATCC No. 53217).

Examples of F$^-$ strains are S∅930 (F) containing plasmid pMF 5534 deposited under ATCC No. 67703 and *E. coli* W31100 (F$^-$) containing plasmid pEFF 920 deposited under ATCC No. 67706.

Examples of *E. coli* strains wherein the deo gene or deo repressors have been deleted are S∅732 which contains plasmid pMF 2005 (ATCC No. 67362), S∅540 which contains plasmid pJBF 5401 (ATCC No. 67359) and S∅930 which contains plasmid pEFF 920 (ATCC No. 67706).

All the *E. coli* host strains described above can be "cured" of the plasmids they harbor by methods well-known in the art, e.g. the ethidium bromide method described by R. P. Novick in *Bacteriol. Review* 33, 210 ( 1969 ) .

The bacterial cell may contain the DNA sequence encoding the ApoE or analog in the body of a vector DNA molecule such as a plasmid. The vector or plasmid is constructed by recombinant DNA techniques so that the sequence encoding the ApoE is incorporated at a suitable position in the molecule.

Plasmids which are used for ApoE analog production can harbor a variety of promoters such as the lambda promoter or the deo promoters.

Among the plasmids which may be used for the production of the ApoE analog are as follows:

A. Plasmid pTVR 590-4 deposited in *E. coli* 12435 (ATCC No. 67360),

B. Plasmid pTVR 279-8 deposited in *E. coli* A1645 (ATCC No. 53216),

C. Any plasmid derived from the above plasmids or from the plasmid pApoE-Ex2 deposited in *E. coli* A1645 (ATCC No. 39787).

D. Any other plasmid which expresses ApoE.

2. Fermentation of cells expressing ApoE analog

We found that bacterial cells expressing the ApoE analog are subject to a "toxic effect" which causes cell lysis soon after ApoE induction. We discovered that protection of the host bacterial cell from this "toxic effect" was achieved by adding to the culture medium an inhibitor of proteolytic digestion of ApoE or analog thereof such as neutralized fatty acids, triglycerides or triglyceride precursors, including any of (i) the fatty acids, e.g. sodium propionate, n-butyric acid (neutralized), and beta-hydroxybutyric acid (neutralized); (ii) the triglycerides, e.g. triacetin, tributyrin and tricaprylin; (iii) the triglyceride precursors, e.g. 1-monomyristoyl-rac-glycerol, 1-monopalmitoyl-rac-glycerol, DL-alpha-hydroxy isovaleric acid and glycerol and (iv) the fatty acid precursor sodium acetate. Butyric acid, beta-hydroxybutyric acid, propionic acid and sodium acetate are preferred and sodium acetate is especially preferred.

The protection of the host cell as described above enabled applicants to employ a long (3 hours) induction period at 42° C. instead of the short (15 minutes) induction period previously disclosed (see coassigned copending U.S. Ser. No. 085,651), and facilitated the scaling up of the fermentation process for industrial production.

While not wishing to be bound by theory we present the following rationale to explain these results. Apolipoproteins are known to interact with lipids and lipid-containing moieties. The "toxic effect" may be explained by the interaction of ApoE with the bacterial cell membrane or by binding of precursors which are important for membrane biosynthesis. If this reasoning is correct the host *E. coli* cell is protected by adding to the medium compounds such as fatty acids, fatty acid precursors, triglycerides or glyceride precursors, with the assumption that they penetrate the cell, bind to ApoE or to other cellular components and thus prevent the ApoE toxicity.

We also found that the aforesaid compounds and also EDTA protect the ApoE protein from proteolytic degradation.

3. Cell Disruption

Surprisingly, we found that adding fatty acids to the medium protected the ApoE analog from degradation by cellular proteases. This was confirmed by in vitro incubation studies, as described in Example 7 and it was therefore decided to add such substances to the buffer during disruption of the cells. Beta- hydroxybutyric acid, butyric acid or n-caproic acid (all neutralized) are preferred as inhibitors of proteolytic degradation of ApoE analog; for reasons of cost and convenience, beta-hydroxybutyrate (sodium salt) is especially preferred.

*E. coli* cells containing recombinant ApoE analog are harvested and disrupted in a buffer containing bivalent cations preferably magnesium ions (10–100 mM) and an inhibitor of proteolytic degradation of ApoE such as beta-hydroxybutyrate at concentrations of 0.1–1%. Any cell disruption method can be used, e.g. sonication, mechanical disruption such as glass bead grinding (Dynomill), or explosion by pressure (Gaulin homogenizer). Under these conditions ApoE analog above is precipitated with the cell debris and is separated from most soluble cytoplasmic components by centrifugation. (See Scheme I and Example 3.)

An alternative aspect of the invention describes production of ApoE analog from the supernatant. The cells are disrupted as described above except that the buffer does not contain magnesium ions; instead the buffer contains a chelating agent such as EDTA.

4. Extraction of ApoE

The pellet containing the ApoE analog is suspended in a buffer containing non-ionic detergent. Preferably the non-ionic detergent is Emulphogen$^R$-BC720 (Sigma) or PEG (9–10) p-t- octylphenol which is sold under the tradename Triton$^R$ X-100 (Merck), designated Triton$^R$. Triton$^R$ was used at a concentration of 0.05–1% preferably 0.3%, at pH between 3.0 and 9.0, preferably 3.0 to 5.0. Under these conditions ApoE analog is selectively extracted from the pellet and is protected from degradation and from formation of aggregates. The extract is neutralized to pH 7.5 and ultrafiltrated.

An optional step before ultrafiltration is to filter the supernatant solution to remove turbidity. This is done particularly with large samples (15 Kg bacterial cake). The preferred filter is the 0.4–1.0 micron depth filter zeta plus 50 SP of Cuno Inc., Industrial Filter Products, 400 Research Parkway, Meriden, Conn. 06450, U.S.A.

5. Ultrafiltration

Any appropriate ultrafiltration method with a cutoff point of about 100K which does not allow ApoE analog to pass through the filter may be used for the fractionation of the ApoE analog. Examples of such methods are Millipore's Pellicon cassette system (the preferred system) or Amicon's hollow fiber system. In all following purification steps there is the novel addition of non-ionic detergent, e.g. Emulphogen$^R$ or Triton$^R$, preferably Triton$^R$, at concentrations of 0.05–1% In the presence of Triton$^R$, ApoE does not cross the membrane; it is separated from low molecular weight components and is dialyzed against the equilibration buffer of the next purification step.

6. Column chromatography methods

A) DEAE SEPHAROSE™

Any weak anion exchange chromatography method can be used in this step but DEAE-SEPHAROSE™ fast flow (Pharmacia) is preferred. Weak anion exchange columns usually have as functional group a tertiary amine (diaminoethyl), but amino ethyl is also possible. The matrix may be based on inorganic compounds, synthetic resins, polysaccharides, or organic polymers; possible matrices are agarose, cellulose, trisacryl, dextran, glass beads, oxirane acrylic beads, acrylamide, agarose/polyacrylamide copolymer (Ultrogel) or hydrophilic vinyl polymer (Fractogel).

The retentate solution from the previous step is chromatographed on a DEAE Sepharose column in buffer, preferably Tris buffer, at a range of pH 7–8, preferably at pH 7.5. ApoE analog is eluted from the DEAE column with salt solution preferably sodium chloride.

The ApoE fraction eluted from the DEAE column has the same molecular weight as ApoE from human plasma when analyzed under the same conditions. This fraction is dialyzed and equilibrated with the buffer used for loading the next column by ultrafiltration dialysis using a 100K membrane as described above in section 4.

B) Q-SEPHAROSE™

Any strong anion exchange (e.g. quaternary amine) method can be used in this step but Q-SEPHAROSE™ (Pharmacia) chromatography is preferred. The functional group of the ion exchange column can be any quaternary amino group such as quaternary amino ethyl and the matrix can be any of the matrices listed hereinabove at paragraph (A). The dialyzed sample from the previous step is loaded on a Q-SEPHAROSE™ column in Tris buffer containing Triton$^R$ at a concentration in a range of 0.1–0.5%, preferably at 0.2% Triton$^R$. At low salt concentrations (up to 100 mM NaCl) an active ApoE fraction containing low levels of endotoxins that has the same pI as plasma ApoE is eluted and is separated from an inactive fraction of ApoE that is eluted at higher salt concentrations (above 200 mM NaCl).

The eluted active fraction of ApoE is dialyzed against the equilibration buffer used for loading the next column by ultrafiltration dialysis using a 100K membrane as described above in section 4.

C) CM-SEPHAROSE™

Any cation exchange (e.g. carboxymethyl) method can be used in this step but CM-SEPHAROSE™ fast flow (Pharmacia) chromatography is preferred. The functional group can be carboxymethyl, a phospho group or sulphonic groups such as sulphopropyl. Possible matrices are listed hereinabove at paragraph (A). The dialyzed sample is chromatographed on CM-SEPHAROSE™ column in sodium acetate buffer pH 4.0–6.0, preferably pH 4.8–5.2, containing 0.2% Triton$^R$ and then washed and eluted with buffer containing 0.05% Triton$^R$. This step enables removal of endotoxins from ApoE resulting in very low endotoxin levels, less than 100 pg endotoxin per mg ApoE analog and usually between about 20 to about 50 pg per mg. In addition, this step reduces the concentration of Triton$^R$ to 0.05%.

7. Triton$^R$ Removal

Triton$^R$ is removed from the above sample by ultrafiltration dialysis using a 100K membrane. Any ultrafiltration method with a cut off point of 100K may be used as described above. Dialysis is carried out against buffers without Triton$^R$ at ApoE concentrations of 0.5 mg/ml to 2 mg/ml and Triton$^R$ concentrations below its critical micelle concentration.

There are three conditions which must prevail during the Triton$^R$ removal step. These are detailed in Example 3G. These conditions allow fast removal of Triton$^R$ while retaining the ApoE in non-aggregated form. The ApoE analog produced is biologically active and very pure. The ApoE analog can then be lyophilized and regain full biological activity on subsequent redissolution.

In a preferred embodiment of step (a) of the above described method the bacterial cell is *Escherichia coli* but other bacterial cells could be used. Further, in the same preferred embodiment, in step (b) the cell wall is disrupted mechanically. Moreover, the separation of cellular debris and insoluble precipitate from the lysate in step (c) comprises centrifugation but other separating methods could be used. Additionally, the non-ionic detergent utilized in the above-described preferred embodiment is Triton$^R$ but other non-ionic detergents could be used.

In a preferred embodiment of step (d) of the above-described method, the treatment step utilized to concentrate and purify the ApoE or analog comprises ultrafiltration, but this could be replaced or complemented by other concentration and filtering methods such as amonium sulfate precipitation, dialysis, freeze-drying or centrifugation. Moreover, the ultrafiltration removes components of molecular weight less than $1 \times 10^5$ daltons. Further, the preferred embodiment of treatment in step (e) comprises chromatography, with the most preferred being ion exchange chromatography. The most preferred embodiment comprises ion exchange chromatography comprising a tertiary amine ligand attached to a resin. After the chromatography step the resulting concentrated, purified ApoE or analog is dialyzed, saving the retentate. The retentate containing the resulting concentrated, purified ApoE or analog are further concentrated and purified by using another chromatography step preferably chromatography comprising a quaternary amine ligand attached to a resin. Following the chromatography step the resulting concentrated, purified ApoE or analog is dialyzed, saving the retentate.

The retentate containing the resulting concentrated, purified ApoE or analog is further concentrated and purified by ion exchange chromatography comprising a carboxy methyl-ligand attached to a resin. The recovery of the concentrated, purified ApoE or analog in step (f) of the preferred method comprises ultrafiltration. The ultrafiltration removes molecules of molecular weight less than $1 \times 10^5$ daltons.

8. An Alternative Embodiment of the Invention:
Purification of ApoE Analog from the Supernatant The present invention additionally provides another method for obtaining a purified recombinant ApoE or polypeptide analog thereof from genetically engineered bacterial cells which produce the recombinant ApoE or polypeptide analog thereof which comprises: (a) culturing the genetically engineered bacterial cells so as to produce the recombinant ApoE or polypeptide analog thereof; (b) treating the bacterial cells in the presence of EDTA so as to obtain a lysate containing soluble recombinant ApoE or polypeptide analog thereof; (c) recovering from the lysate a solution containing soluble recombinant ApoE or polypeptide analog thereof; (d) treating the solution so recovered with a solution containing a non-ionic detergent to obtain a second solution containing solubilized recombinant ApoE or polypeptide analog thereof; (e) treating the second solution containing recombinant ApoE or polypeptide analog thereof so as to concentrate and purify the recombinant ApoE or polypeptide analog thereof; and (f) recovering the resultant concentrated purified recombinant ApoE or polypeptide analog thereof.

The extraction of ApoE analog from the supernatant is similar to that described for extraction from the pellet but the following points must be noted:

i) Extraction with Triton$^R$ is similar except the preferred pH is 4.0–4.5.

ii) Ultrafiltration is as described hereinabove and serves the same function.

iii) DEAE SEPHAROSE™ Chromatography

DEAE SEPHAROSE™ (weak anion) chromatography separates the ApoE analog into two fractions. At low salt concentrations (up to about 80 mM NaCl) an active ApoE fraction containing low levels of endotoxins that have the same pI as plasma ApoE is eluted and is separated from an inactive fraction of ApoE analog that contains a high endotoxin level that is eluted at high salt concentration (above 150 mM NaCl). Thus, the weak anion DEAE- chromatography step functions in Scheme II as the Q-SEPHAROSE™ step in Scheme I.

d) Heparin-SEPHAROSE™ Chromatography

Any affinity exchange chromatography method with a functional group that binds ApoE can be used in this step, e.g. dextran sulphate or chondroitin sulphate, but heparin is preferred. The matrix used can be any of the matrices listed above in section 6 for use in purifying ApoE from the pellet. However, SEPHAROSE™ is the preferred matrix. The buffer containing Triton$^R$ can be in the pH range 6.5 to 9.5 but pH of about 7.0 is preferred as giving a higher loading capacity of ApoE analog. This step removes *E. coli* protein impurities and endotoxins resulting in very low levels of endotoxin (about 60 pg/mg).

iv) CM-SEPHAROSE™ and Triton$^R$ Removal Steps

These steps have the same purpose and operate under similar conditions as in the preferred embodiment for purification of ApoE from the pellet.

In a preferred embodiment of the above-described method for purifying ApoE or an analog thereof from bacterial cell supernatant the bacterial cell in step (a) is preferably *Escherichia coli* but other bacteria may be used. The cell wall in step (b) is disrupted e.g. mechanically. Further, the separation of cellular debris and insoluble precipitate from the cell supernatant in step (c) comprises centrifugation but other methods of separating may be used. Additionally, the non-ionic detergent utilized throughout the method for purifying ApoE or an analog thereof from bacterial cell supernatant is preferably Triton$^R$; alternatively, the non-ionic detergent is Emulphogen$^R$. Further, the treatment in step (d) to concentrate and purify ApoE or analog comprises preferably ultrafiltration but other concentration and filtering methods could be used. The ultrafiltration removes molecules of molecular weight less than $1 \times 10^5$ daltons.

Further, the preferred embodiment of treatment in step (e) comprises chromatography with the most preferred comprising ion exchange chromatography. The most preferred ion exchanger is a tertiary amine ligand attached to a resin. Following the chromatography step the resulting concentrated, purified ApoE or analog is dialyzed, saving the retentate. The retentate containing the resulting concentrated, purified ApoE or analog is further concentrated and purified preferably by affinity exchange chromatography wherein the most preferred affinity exchanger is a heparin ligand attached to a resin. The resulting concentrated, purified ApoE or analog is dialyzed, again saving the retentate. The retentate containing the resulting more concentrated, purified ApoE or analog is further concentrated and purified preferably by cation exchange chromatography wherein the most preferred cation exchanger is a carboxymethyl ligand attached to a resin. Further, the recovery of the concentrated, purified ApoE or analog in step (f) preferably comprises ultrafiltration which removes molecules of molecular weight less than $1 \times 10^5$ daltons but other methods of concentration and filtering could be used.

Additionally, the invention provides a composition comprising ApoE or analog thereof produced by the above-described methods and a suitable carrier and also provides a composition comprising such ApoE which contains or is linked physically to a chemotherapeutic or radiotherapeutic or radiodiagnostic agent and a suitable carrier.

Further, the present invention provides a method of treating a subject suffering from atherosclerosis which comprises administering to the subject an amount of ApoE or analog thereof effective to combat atherosclerosis. As used herein atherosclerosis means a variable combination of changes in the intima of arteries consisting of the focal accumulation of lipids, complex carbohydrates, blood and blood products, fibrous tissue, and calcium deposits, and associated with medial changes.

Additionally, the invention provides a method of treating a subject suffering from hypercholesterolemia caused by impaired cholesterol metabolism which comprises administering to the subject an amount of ApoE or analog thereof effective to normalize cholesterol metabolism so as to alleviate hypercholesterolemia and thereby treat the subject. As used herein hypercholesterolemia means an excess of cholesterol in the blood.

The present invention further provides a method of treating a subject suffering from hyperlipoproteinemia caused by impaired lipid metabolism which comprises administering to the subject an amount of ApoE or analog thereof effective to normalize lipid metabolism so as to alleviate hyperlipoproteinemia and thereby treating the subject. As used herein hyperlipoproteinemia means an excess of lipoproteins in the blood.

Additionally, the invention provides a method of treating a subject suffering from neuronal injury which comprises administering to the subject an amount of ApoE or analog thereof effective to promote nerve development and regeneration.

Furthermore the invention provides a method of treating a subject suffering from a tumor which harbors high levels of LDL receptor which comprises administering to the subject an amount of ApoE or analog thereof which contains or is linked physically to a chemotherapeutic or radiotherapeutic agent effective to treat the tumor.

Additionally the invention provides a method of diagnosis of LDL receptor defects in a subject by administering to the subject an amount of ApoE or analog thereof which contains or is linked physically to a radiodiagnostic agent effective to quantitate the LDL receptors.

Furthermore the invention provides a method of diagnosis of primary or secondary sites of tumor growth in a subject where the tumor harbors high levels of LDL receptors which comprises administering to the subject an amount of ApoE or analog thereof which contains or is linked physically to a radiodiagnostic agent effective to visualize the tumor.

Furthermore the invention provides a method of treatment of autoimmune disease in a subject which comprises administering to the subject an amount of ApoE or analog thereof effective to treat the subject.

Furthermore the invention provides a method of treatment of a subject having an immunodeficient disease which comprises administering to the subject an amount of ApoE or analog thereof effective to treat the subject.

In addition the invention provides a lipid emulsion comprising ApoE or analog thereof wherein the ApoE or analog thereof is a ligand, and the use of such lipid emulsion for drug delivery and tissue targeting.

The invention further provides a method for increasing the production of ApoE or analogs thereof in a bacterial host by adding to a medium in which the host is growing an effective amount of compounds selected from the group consisting of neutralized fatty acids, fatty acid precursors, triglycerides, triglyceride precursors and acetate. In a preferred embodiment of the invention the neutralized fatty acid is sodium propionate, n-butyric acid, or beta-hydroxybutyric acid. In another preferred embodiment of the invention the triglyceride is triacetin, tributrin or tricaprylin. In a further preferred embodiment of the invention the triglyceride precursor is 1-mono myristol-lac-glycerol, 1-mono-palmityl-lac-glycerol, DL-α-hydroxy isovaleric acid or glycerol. In a most preferred embodiment of the invention the added compound is acetate, preferably sodium acetate at a concentration of about 0.1%–1% and the preferred concentration is about 0.5%. The preferred concentration in the culture of fatty acid, triglyceride or triglyceride precursor is about 0.1%–0.5%, and the preferred concentration is about 0.2%.

Finally, the invention provides a method of protecting ApoE protein in solution from degradation by adding to the solution an effective amount of a compound selected from the group consisting of neutralized fatty acids, fatty acid precursors, triglycerides, triglyceride precursors, acetate and EDTA. In one embodiment of the invention, the effective amount of compound added to the solution produces a concentration of compound in the solution of about 0.1% to 0.5%, preferably about 0.2%.

The methods of the present invention will be better understood by reference to the following experiments and examples, which are provided for purposes of illustration and are not to be construed as in any way limiting the scope of the invention, which is defined by the claims appended.

EXAMPLE 1

Host-Vector System For ApoE Analog Expression

Figure 3:
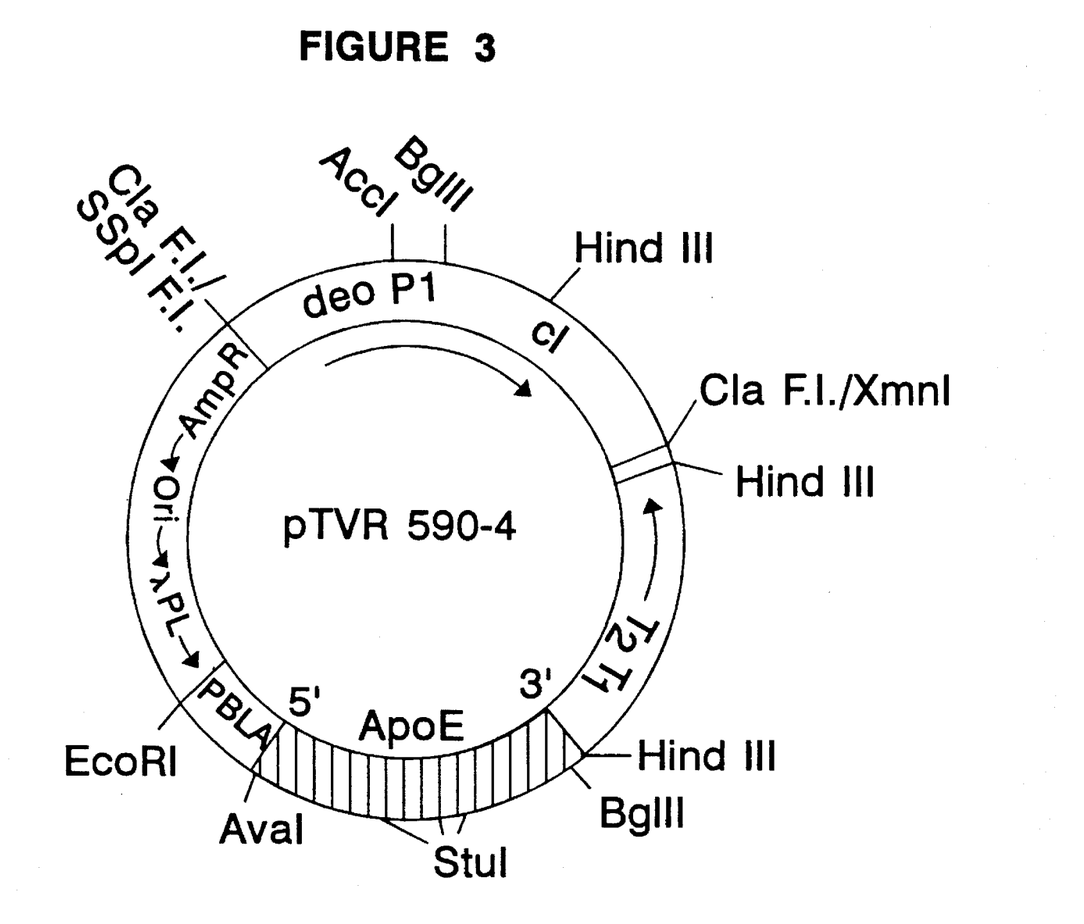
FIG. 3: Production of plasmid pTVR 590-4

The preferred host-vector system used for production of the ApoE analog met-ApoE is *E. coli* strain ATCC No. 12435 harboring plasmid pTVR590-4; this host-vector system, shown in FIG. 3, has been deposited with the American Type Culture Collection (ATCC) in Rockville, Md. under ATCC Accession No. 67360.

The construction of plasmid pTVR 590-4 which is described below has been fully described in co-assigned copending patent application, EPO Publication No. 303,972 (Example 11 and FIG. 27). Plasmid pTVR 590-4 contains the following elements:

a) Origin of replication.

b) The $Amp^R$ gene in counter clockwise orientation.

c) In clockwise orientation and in 5' to 3' order, a truncated deo P1 promoter sequence and the lambda $cI^{857}$ temperature-sensitive repressor coding sequence.

d) In counterclockwise orientation and in 5' to 3' order, the lambda promoter, the beta lactamase promoter-ribosomal binding site, the coding sequence for ApoE analog and the $T_1T_2$ transcription termination sequences.

This plasmid is a high level expressor of ApoE analog protein under the control of the strong leftward promoter of bacteriophage lambda ($P_L$) which is thermoinducibly controlled by the constitutively expressed $cI^{857}$ temperature-sensitive repressor also situated on the plasmid. Production of ApoE analog protein from this plasmid takes place only on heat-induction at 42° C.

This is a so-called "host independent" expression system since the plasmid can thermoinducibly produce the met-ApoE analog independent of prior insertion of the lambda $cI^{857}$ gene into the host *E. coli* chromosome. This plasmid can therefore be used to transform a wide variety of host bacterial cells. The host described, ATCC No. 12435, is a prototrophic wild-type strain of *E. coli* freely obtainable from the ATCC collection.

EXAMPLE 2

Growth of *E. coli* ATCC Accession No. 12435 harboring plasmid pTVR 590-4 and production of bacterial cake containing ApoE analog The following description of the fermentation of *E. coli* producing ApoE analog is the preferred embodiment for production of cell cake containing ApoE analog.

1. Seed Flask Development

The contents of frozen vials containing *E. coli* ATCC No. 12435/pTVR 590-4 (Example 1) are used to inoculate seed flasks containing the following medium:

| | |
|---|---|
| $K_2HPO_4$ | 9 g |
| $KH_2PO_4$ | 1 g |
| NaCl | 5 g |
| $MgSO_4.7H_2O$ | 0.2 g |
| $NH_4Cl$ | 1 g |
| $FeNH_4$ citrate | 0.01 g |
| Trace elements solution | 1 ml |
| Biotin | 0.5 mg |
| Glucose | 5 g |
| Ampicillin, sodium salt | 0.1 g |
| Deionized water | 1 L |

Trace elements stock solution:

| | |
|---|---|
| $MnSO_4.H_2O$ | 1 g |
| $ZnSO_4.7H_2O$ | 2.78 g |
| $CoCl_2.6H_2O$ | 2 g |
| $Na_2MoO_4.2H_2O$ | 2 g |
| $CaCl_2.2H_2O$ | 3 g |
| $CuSO_4.5H_2O$ | 1.85 g |
| $H_3BO_3$ | 0.5 g |
| Concentrated HCl | 100 mL |
| Deionized Water | 900 mL |

Glucose and ampicillin are added from sterile concentrated stock solutions after autoclaving the other components of the medium. The cultures are incubated at 30° C. overnight on a rotary shaker at 250 rpm, and reach an $O.D_{660}$ of 3.5–5.0.

2. Seed Fermenter

The contents of the seed flask are used to inoculate a 50 L seed fermenter containing 25–30 L of the following production medium, which contains per liter:

| | |
|---|---|
| $K_2HPO_4$ | 8 g |
| $KH_2PO_4$ | 2 g |
| Sodium citrate | 2 g |
| $NH_4Cl$ | 2 g |
| $FeNH_4$ citrate | 0.02 g |
| $CaCl_2.2H_2O$ | 0.04 g |
| $K_2SO_4$ | 0.6 g |
| Trace elements solution (as in Section 1) | 3 mL |
| Antifoam (Silicolapse 5000) | 2 mL |

| Added after sterilization (per liter of medium) | | |
|---|---|---|
| $MgSO_4.7H_2O$ | | 0.4 g |
| Sodium ampicillin | | 0.1 g |
| Glucose | | 40–60 g |
| $NH_3$ (25–28% in water) | approx. | 40 mL |

Glucose is added batchwise at inoculation; ammonia is automatically added for pH control (set point pH=7.0) during growth.

The culture is cultivated at 30° C. for 15–20 hours in order to achieve growth; the $O.D_{660}$ generally reaches 20–30 during this time. This is equivalent to a dry cell weight (DCW) of 7.5–12 g/L.

3. Production Fermenter

The contents of the seed fermenter are used to inoculate a 750 L (nominal volume) fermenter containing about 360 L production medium as described for seed fermentor, but excluding ampicillin. The culture is cultivated at 30° C. until an $O.D_{660}$ of 10 is obtained. Induction of ApoE analog expression is then achieved by raising the fermenter temperature to 42° C. At induction, the following are added to the fermenter:

| | |
|---|---|
| DL-methionine | 0.6 g per L of medium |
| Sodium acetate | 5 g per L of medium |

The sodium acetate (0.1%–1%) is added to protect cells from the "toxic effect" caused by the ApoE analog.

The fermenter temperature is maintained at 42° C. for three hours, at which time the cells are harvested. The $O.D_{660}$ of the cell suspension at harvest is generally 16–20, the volume is 400–430 L and the DCW is 5.0–6.5 g/L.

4. Harvest of Cells

The cell suspension is centrifuged at 14,000 rpm (16,000 g) in a CEPA 101 tubular bowl centrifuge at a feed rate of 250 L/hr, and a cell cake weighing about 10 Kg is produced and saved. Alternatively, the cell suspension is centrifuged in a Westfalia CSA-19 continuous centrifuge at 500 L/hr. The sludge is either disrupted immediately or frozen.

In both cases the supernatant contains no detectable ApoE analog as measured by SDS-polyacrylamide gel electrophoresis.

EXAMPLE 3

Improved Method for Purification of Recombinant ApoE Analog

The following method is suitable for scale-up for industrial application and yields a very pure ApoE analog. The general scheme of the downstream process (Scheme I) consists of steps A through G as follows:

Scheme I. Downstream Processing of the Recombinant Human ApoE Analog Extracted from the Pellet

A CELL DISRUPTION IN PRESENCE OF MAGNESIUM IONS.

B EXTRACTION OF CELL PELLET WITH TRITON$^R$.

C 100K ULTRAFILTRATION.

D DEAE CHROMATOGRAPHY

E Q SEPHAROSE™ CHROMATOGRAPHY

F CM SEPHAROSE™ CHROMATOGRAPHY

G 100K ULTRAFILTRATION—TRITON$^R$ REMOVAL.

The following detailed example of the steps in purification of the ApoE analog is an example involving 3 Kg cell cake. In addition we have successfully processed a 15 Kg cell cake using the methods described below with only minor modifications involving scale-up in the size of the equipment used.

Steps A through D were performed on 2 batches of bacterial cake, each weighing 1.5 Kg. After step D, the two batches were combined and processed as one batch through steps E to G. Steps A, B, C were performed at 4° C.–10° C., except where otherwise indicated. All other activities were performed at room temperature.

A. CELL DISRUPTION IN PRESENCE OF MAGNESIUM IONS 1.5 Kg of wet cell cake was suspended in 6 L of buffer A which consists of 50 mM tris/HCl, 30 mM $MgCl_2$, 0.25% beta hydroxybutyrate sodium salt, pH=7.5. (The beta hydroxybutyrate was added as a protease inhibitor; see Example 7.) This was then homogenized using a Kinematica homogenizer yielding 7.5 L of homogenate. Disruption was then performed using a Dynomill KDL bead mill disrupter (Willy A. Bachofen, Basel) at 5 L/hr (in two cycles). Three-fold dilution of the resulting suspension using buffer A yielded a volume of 22.5 L. This lysate contained about 6 g ApoE analog, i.e. about 4 g ApoE analog per Kg of original bacterial cake.

Centrifugation was then performed in a continuous CEPA-41 tubular bowl centrifuge, (Carl Padberg, Lahr/Schwarzwald) with a feed rate of 9 L/hr at 20,000 rpm (17,000 g). The pellet, weighing approximately 700 g and containing the insoluble ApoE analog was saved and the supernatant was discarded. (Note that the ApoE is insoluble due to the presence of $Mg^{++}$ ions.)

B. EXTRACTION OF CELL PELLET WITH TRITON$^R$

Six liters (1:10) of extraction buffer were added to the pellet. (Extraction buffer: 50 mM tris/HCl, 20 mM EDTA, 0.3% Triton$^R$, pH adjusted to 3.0 with HCl). Suspension was achieved using a homogenizer (Kinematica) at low speed. Then another 6 L extraction buffer was added (giving a final pellet:buffer ratio of 1:20) and the pH was adjusted to 4.5 with 1N NaOH. The resulting 12 L suspension was incubated for 10 minutes at room temperature with stirring.

After incubation, the suspension was centrifuged on the CEPA 41 Centrifuge at a feed rate of 20 L/hr. The pellet weighing about 450 g was discarded and the supernatant solution containing ApoE analog was titrated to pH=7.5 with 1N NaOH and saved.

Note: Triton$^R$ is present in all following steps and is removed in step G.

C. 100K ULTRAFILTRATION

The purpose of this step is to remove low molecular weight contaminants by ultrafiltration/dialysis.

A Millipore Pellicon ultrafiltration system using one 100K cassette type PTHK was utilized to concentrate the supernatant of the previous step (about 12 L) to about 2 L. The feed pressure was 20 psig and the filtrate flow rate was 20 L/hr. The dialysis buffer was 50 mM tris HCl, 10 mM EDTA and 0.1% Triton$^R$, pH=7.5. The 2 L retentate containing about 2–3 mg ApoE analog/ml was kept cool with ice.

The retentate was dialyzed using the recirculating mode of the Pellicon ultrafiltration system until a filtrate conductivity equivalent to that of the dialysis buffer was obtained; this was the criterion used throughout the purification for termination of dialysis.

D. DEAE CHROMATOGRAPHY

The purpose of this step is to separate the ApoE analog from contaminants such as proteins and other cellular materials. In this step a 1.6 L DEAE SEPHAROSE™ Fast Flow column (Pharmacia) was used. The flow rate was 10 column volumes/hr. The capacity of the column under these conditions was determined to be 4 mg ApoE/ml. The column was first equilibrated with DEAE equilibration buffer: 20 mM tris/HCl, 1 mM EDTA, 0 5% Triton$^R$, pH=7.5.

The retentate solution from the previous step (about 3 L) was then loaded on the column and washed with 3 column volumes (CV) of equilibration buffer. The first elution was performed using 3 CV of equilibration buffer containing 120 mM NaCl. Fractions were collected and the progress of the run was monitored by continuously following the absorbance of the eluate at 280nm. The fractions were analyzed by SDS polyacrylamide gel electrophoresis stained by Coomassie Blue and the trailing edge of the peak (3.1 CV) was saved.

The second elution was performed using the equilibration buffer containing 150mM NaCl. Fractions were collected and analyzed by SDS gel electrophoresis and most of the peak (3.9 CV) was saved. Endotoxins were measured by the Limulus AmebocyteLysate (LAL) assay described in U.S. Pharmacopeia (U.S.P.) XXI, 1165–1166 (1985). The level of endotoxin was 3 µg per mg ApoE analog.

Concentration and dialysis after DEAE-Sepharose

The fractions indicated from the first and second eluates were pooled and dialyzed using the Pellicon ultrafiltration system, with one 100K cassette; the dialysis buffer was 20 mM tris/HCl, 1 mM EDTA, 0.1% Triton$^R$, pH=7.5. The sample was concentrated to 2 L (about 2–3 mg ApoE/ml) and dialyzed.

E. Q-SEPHAROSE™ (QS) CHROMATOGRAPHY

The purpose of this step is to separate the active from the inactive ApoE analog and to further remove endotoxins.

In this step a 1.6 L QS Fast Flow Column (Pharmacia) was used; the column capacity under these conditions was about 7 mg ApoE/ml and the flow rate was about 10 CV/hr.

The QS equilibration buffer was 20 mM tris/HCl, 1 mM EDTA, 0.2% Triton$^R$, pH=7.8. After equilibration, the retentate solutions from two batches of the previous step were combined and loaded on to the column, i.e. a total volume of about 5 L of buffer containing about 5 g ApoE analog. The column was then washed with 2.8 CV of equilibration buffer. The first elution was performed with 3 CV of equilibration buffer containing 20 mM NaCl and the second elution was performed with about 5.5 CV of equilibration buffer containing 40 mM NaCl. Fractions were collected, monitored and analyzed as described above, and 2.0 CV were combined and saved. The level of endotoxin was measured by the LAL assay and was now less than 250 pg/mg ApoE analog.

Two subsequent elutions using buffer containing 70 mM NaCl and 350 mM NaCl respectively eluted the inert ApoE analog.

Concentration and dialysis after Q-Sepharose

The QS-derived saved pooled fractions were concentrated and dialyzed by ultrafiltration through a Millipore Pellicon Ultrafiltration system using one 100K cassette.

The dialysis buffer was 10 mM tris/HCl, 1 mM EDTA, 0.1% Triton$^R$, pH=7.5. The sample was dialyzed using the recirculating mode whilst maintaining the ApoE concentration at 2–3 mg/ml. The final retentate volume was about 500 ml.

F. CM-SEPHAROSE™ CHROMATOGRAPHY

The purpose of this step is to further remove endotoxins and to lower the concentration ok Triton$^R$ to 0.05%.

In this step a 120 ml CM-SEPHAROSE™ Fast Flow (Pharmacia) column was used. The equilibration buffer was 20 mM Na acetate, 1 mM EDTA, 0.2% Triton$^R$, pH=4.8. After equilibration, the retentate solution from the previous step was loaded on to the CM-SEPHAROSE™ column. The capacity of the column was 10 mg ApoE/ml and the flow rate was 10 CV/hr.

The column was then washed with the following solutions: 4 CV of equilibration buffer followed by 5 CV of equilibration buffer containing 70 mM NaCl followed by 2 CV of 20 mM Na acetate, 1 mM EDTA, 0.05% Triton$^R$, 70 mM NaCl pH=4.8. The eluate from the loading and washing steps was discarded.

The column was then eluted. The eluent was 8 CV of 20 mM Na acetate, 1 mM EDTA, 0.05% Triton$^R$, 300 mM NaCl, pH=5.0. The progress of the elution was monitored by continuously following the absorbance of the eluate at 280 nm. (Two different base lines are used during the elution: one is the high U.V. absorbance buffer containing 0.2% Triton, the other is the low U.V. absorbance buffer containing 0.05% Triton. The use of a sensitivity scale of about 1.0 OD allows both buffers to appear on the chart column, the low at the foot and the high at about 0.5 OD.)

The sample containing the ApoE analog was immediately titrated to pH 7.8 and saved. The endotoxin level in this sample was below 50 pg per mg ApoE analog as measured by the LAL assay.

G. 100K ULTRAFILTRATION—TRITON$^R$ REMOVAL

The purpose of this step is to remove the Triton$^R$.

This step was carried out at 4° C. using the Millipore Pellicon Ultrafiltration System, containing one 100K cassette, pre-washed with 0.5M NaOH overnight. The flow rate was 9–12 L/hr and the inlet/pressure was 5–10 psig. (This low flow rate is used to prevent aggregation of the ApoE analog as the Triton$^R$ is being removed.) The ApoE sample from the previous step (960 ml containing about 600 mg ApoE analog) was diluted to 0.5 mg/ml with 10 mM NaHCO$_3$ buffer pH=7.7.

The sample was then treated in the ultrafiltration system and the following conditions were applied throughout this Triton$^R$ removal step:

a) The Triton$^R$ concentration must be lower than 0.02% i.e. the Triton$^R$ concentration must be below its critical micelle concentration in order to achieve effective Triton$^R$ removal across the 100K membrane.

b) The ApoE analog must not be diluted below 0.5 mg/ml or dissociation of the ApoE molecule will occur and it may cross the 100K membrane.

c) The ApoE analog must not be concentrated above 1.5 mg/ml or aggregation of the ApoE molecules may occur.

The dialysis buffer used in the ultrafiltration system was 10 mM NaHCO$_3$, 150 mM NaCl, pH=7.8.

After concentration and dilution steps in accordance with the above conditions, the dialysis was performed at constant volume and constant flow rate and the dialysis was completed when the absorbance at 280 nm of the filtrate was 0.01 units. (Triton$^R$ solution absorbs at 280 nm and an absorbance of 0.01 is equivalent to 0.0005% Triton$^R$.) The total volume of final retentate was 770 ml and the total volume of the filtrate was 9.5 L.

The solution containing the ApoE analog was then filtered (0.2 micron filter) and stored at −70° C. in 80 ml glass bottles.

Overall Yield:

0.3 g of highly purified ApoE analog were recovered from 3 Kg of bacterial cake. The ApoE analog, approximately 97% pure, was in the same aggregation state as plasma ApoE when tested under the same conditions of gel permeation analysis. The ApoE analog sample contained less then 50 pg of endotoxins/mg protein.

Lyophilization

If the ApoE analog is to be lyophilized the dialysis buffer in the Triton$^R$ removal step is 2 mM NaHCO$_3$, pH=7.8, and after lyophilization the samples of ApoE analog are stored at −20° C.

After lyophilization the ApoE analog can be redissolved and it retains its normal biological activity. The lyophilized ApoE analog is very stable for at least a year.

EXAMPLE 4

Alternative Improved Method For Purification Of Recombinant ApoE

This method is a process for production of highly purified ApoE analog from the cell supernatant and it is suitable for scale-up for industrial application. The general scheme of the downstream process (Scheme II) consists of A' through G' as follows:

A' CELL DISRUPTION—NO MAGNESIUM IONS PRESENT.

B' EXTRACTION OF SUPERNATANT WITH TRITON$^R$.

C' 100K ULTRAFILTRATION.

D' DEAE CHROMATOGRAPHY

E' HEPARIN-SEPHAROSE™ CHROMATOGRAPHY

F' CM SEPHAROSE™ CHROMATOGRAPHY

G' 100K ULTRAFILTRATION—TRITON$^R$ REMOVAL.

The following detailed example of the steps in purification of the ApoE analog from the supernatant is an example involving 1.5 Kg cell cake. The method described is suitable for scale-up with only minor modifications.

A bacterial cake weighing 1.5 Kg from one or more fermentations was processed downstream through steps A' to G'. Steps A', B', C' and G' were performed at 4° C.–10° C., except where otherwise indicated. All other activities were performed at room temperature.

A'. Cell Disruption 1.5 Kg of wet cell cake (containing about 6 g ApoE analog) was suspended in 6 L of buffer EB. (Buffer EB=50 mM tris/HCl, 10 mM EDTA, 0.25% beta hydroxybutyrate sodium salt, pH=7.5)

The suspension was homogenized using a Kinematica homogenizer yielding 7.5 L of homogenate. Disruption was then performed by glass bead grinding (KDL Dynomill) at 5 L/hr (in two cycles). Three-fold dilution of the resulting suspension using buffer EB yielded a volume of 22.5 L.

Centrifugation of this lysate was then performed in a continuous CEPA-41 tubular bowl centrifuge, with a feed rate of 9 L/hr. The pellet, weighing approximately 600 g was discarded, and the supernatant (about 22 L) containing the soluble ApoE analog was saved.

B'. Extraction of Cell Pellet with Triton$^R$

Triton$^R$ was added to the supernatant of the previous step to a final concentration of 0.3%. The resulting suspension was then acidified with HCl to pH=4.0 and centrifuged on a Sorval centrifuge for 5' at 4500 rpm. The pellet weighing about 1,200 g was discarded. The supernatant solution (19.8 L), containing the ApoE analog, was titrated to pH 7.5 and saved.

Note: Triton$^R$ is present in all following steps until it is removed in step G'.

C'. 100K Ultrafiltration

The purpose of this step is to remove low molecular weight contaminants by ultracentrifugation/dialysis.

The Millipore Pellicon ultrafiltration system using one 100K cassette was utilized to concentrate the supernatant of the previous step to about 12 L. The feed pressure was 20 psig and the dialysis buffer was 20 mM tris/HCl, 1 mM EDTA and 0.1% Triton$^R$, pH=7.5. The 12 L retentate was dialyzed as described in step C, Scheme I; ApoE analog concentration in the retentate was maintained at 2–3 mg/ml. The dialysis yielded about 7.5 L of retentate which contained about 5–10 μg endotoxins per mg ApoE analog as measured by the LAL assay.

D'. DEAE Chromatography

The purpose of this step is to separate the ApoE analog from contaminants such as proteins and other cellular materials. In addition, separation of active ApoE analog from inactive ApoE analog and from endotoxins is achieved.

Six runs through a 400 ml column of DEAE Fast Flow column (Pharmacia) were performed. The flow rate was 10 CV/hr. The capacity of the DEAE column under these conditions was 4 mg ApoE/ml. The column was first equilibrated with equilibration buffer: 20 mM tris/HCl, 1 mM EDTA, 0.5% Triton$^R$, pH=7.5.

One sixth of the retentate solution from step C' was loaded each time and the column was washed with 3 CV of equilibration buffer. The first elution was performed using 3.6 CV of equilibration buffer containing 20 mM NaCl and the eluate was discarded. The second elution was performed using about 3.2 CV of equilibration buffer containing 80 mM NaCl. The progress of the run was monitored by continuously following the absorbance of the eluate at 280 nm. Fractions were collected from each run and were analyzed by SDS polyacrylamide gel electrophoresis stained by Coomassie Blue. The front of the peak containing a high amount of impurities was discarded and the rest of the peak was saved; it contained about 100–300 ng endotoxins per mg ApoE analog. Two subsequent elutions using equilibration buffer containing 110 mM NaCl and 215 mM NaCl respectively eluted the inert ApoE analog.

Concentration and Analysis After DEAE-SEPHAROSE™

The saved eluates from the 6 column runs were pooled (total volume=6.8 L) and dialyzed using the Pellicon ultrafiltration system, with one 100K cassette (type PTHK, Millipore). The dialysis buffer was 20 mM Tris, 1 mM EDTA, 0.1% Triton$^R$, pH=7.0. The flow rate of the filtrate was 20 L/hr and the inlet pressure was 20 psig. The dialysis yielded about 2 L of retentate solution containing the ApoE analog.

E'. Heparin-SEPHAROSE™ Chromatography

Heparin-SEPHAROSE™ binds ApoE analog effectively. The Heparin-SEPHAROSE™ was prepared as described by K. H. Weisgraber and R. W. Mahley. J. Lipid Res. 21, 316–325 (1980). The purpose of this chromatographic step is to purify ApoE analog from *E. Coli* protein impurities and from endotoxins, resulting in a very low endotoxin level (about 60 pg/mg) In this step and through to step G', half the sample obtained from the previous step was processed.

A 300 ml Heparin-SEPHAROSE™ CL 6B column was used; the capacity at pH 7.0 is 4 mg ApoE analog/ml SEPHAROSE™ and the flow rate was about 5 CV/hr.

The equilibration buffer was 20 mM tris/HCl, 1 mM EDTA, 0.2% Triton$^R$, pH=7.0. After equilibration, the retentate solution from step D' was loaded on to the column, i.e. a total volume of about 1 L of buffer containing about 1 g ApoE analog. The column was then washed with 1.5 CV of equilibration buffer and then with 4 CV of pH=8.0 buffer which is 20 mM tris/HCl, 1 mM EDTA, 0.2% Triton$^R$, pH 8.0. The first elution was performed with 1.5 CV of pH 8 buffer containing 50 mM NaCl. The second elution was performed with about 1 CV of pH=8.0 buffer containing 500 mM NaCl.

The fractions were monitored and analyzed as described above and the second eluate was saved, diluted twofold in pH=8.0 buffer and stored at −20° C. The concentration of endotoxins in this sample was about 60 pg endotoxins per mg ApoE analog.

Concentration and dialysis after Heparin-SEPHAROSE™

The stored sample was thawed and then concentrated and dialyzed by ultrafiltration through a Millipore Pellicon system, using one 100K cassette.

The dialysis buffer was 10 mM tris/HCl, 1 mM EDTA, 0.1% Triton$^R$, pH=7.5. The sample was concentrated and dialyzed by repeated dilution and subsequent concentration to maintain the ApoE concentration at 2–3 mg/ml. The final retentate volume was saved.

F'. CM SEPHAROSE™ CHROMATOGRAPHY

The purpose of this step and the conditions of operating it are similar to those of Scheme I, step F, i.e. to remove residual endotoxins, and to lower the concentration of Triton$^R$ to 0.05%.

In this step a 120 ml CM SEPHAROSE™ Fast Flow column (Pharmacia) was used. The equilibration buffer was 20 mM Na acetate, 1 mM EDTA, 0 2% Triton$^R$, pH=4.8. After equilibration, the retentate solution from the previous step was acidified to pH=4.8 and loaded on to the CM-SEPHAROSE™ column. The capacity of the column was 10 mg ApoE analog/ml of SEPHAROSE™ and the flow rate was 10 CV/hr.

The column was then washed with the following solutions: 3 CV of equilibration buffer followed by 6.6 CV of equilibration buffer containing 70 mM NaCl followed by 5 CV of 20 mM Na acetate, 1 mM EDTA, 0.05% Triton$^R$, 70 mM NaCl pH=4.8.

The column was then eluted. It is important for the next step that the ApoE fractions collected are not diluted below 1 mg/ml. The eluent was about 6 CV of 20 mM Na acetate, 1 mM EDTA, 0.05% Triton$^R$, 300 mM NaCl pH=5.0. The eluate, containing the ApoE analog, was immediately titrated to pH=7.5 and saved; it was stored at −20° C. The amount of endotoxins in this sample was found to be less than 30 pg per mg ApoE analog.

G'. Ultrafiltration—Triton$^R$ Removal

The purpose of this step, to remove the Triton$^R$, is the same as in Step G, Scheme I (Example 3) and is carried out under similar conditions.

This step was carried out using the Millipore Pellicon Ultrafiltration System with one 100K cassette pre-washed with 0.5M NaOH overnight. The flow rate was 10 L/hr and the inlet pressure was 5 psig; this lower flow rate is used to prevent aggregation of the ApoE analog as the Triton$^R$ is being removed. The dilution buffer is 10 mM NaHCO$_3$ pH=7.8.

The sample was then treated in the ultrafiltration system and the same three conditions applied throughout this Triton$^R$ removal step as recited in step G in Scheme I. The dialysis buffer used in the ultrafiltration system was 2 mM NaHCO$_3$, pH=7.8.

After concentration and dilution steps in accordance with the above conditions, the dialysis was performed and was completed when the absorbance at 280 nm of the filtrate was 0.016. The retentate contained about 0.5 mg/ml of ApoE analog. The solution containing the ApoE analog was then filtered (0.2 micron filter).

Overall Yield: 0.9 g of highly purified ApoE analog were recovered from 1.5 Kg of bacterial cake. The ApoE analog, approximately 93% pure, was in the same aggregation state as plasmatic ApoE under the same conditions of gel permeation analysis and contained less than 30 pg endotoxins per mg. (Endotoxin was assayed as described in Example 3).

The samples of ApoE analog were lyophilized and stored at −20° C. This ApoE analog prepared from-the cell supernatant behaves in a similar fashion after lyophilization to ApoE analog prepared from the cell pellet. It can be redissolved in water and retains its normal biological activity.

EXAMPLE 5

Characterization of ApoE Produced By the Improved Method

Two batches (01 and 02) of ApoE analog produced by two different fermentations and purified by the methods described above in Scheme I (Example 3) were analyzed and compared to naturally occurring ApoE prepared from human plasma (p-ApoE).

A. Purity and Homogeneity

The purity of the r-ApoE was approximately 97% of the total protein as estimated from Coomassie blue and silver staining of SDS-PAGE.

The protein identified as ApoE and which comprises 97% of the total protein includes, in addition to the main band, a band of approximately 10–15% of the total protein that appears just below the main band of ApoE. This band is identified as a partially cleaved ApoE as determined by Western blot and by N-terminal amino acid sequence analysis (see Section B.5 below).

Residual DNA and RNA were estimated by measuring the ratio of absorbance at 280 to 260 nm in a sample of ApoE, using p-ApoE as a reference material (Table I).

TABLE I

| Sample | $A_{280}/A_{260}$ |
| --- | --- |
| p-ApoE | 1.74 |
| r-ApoE (Batch 01) | 1.74 |
| r-ApoE (Batch 02) | 1.78 |

The value of the $A_{280}/A_{260}$ ratios indicates that contamination by nucleic acids is below detection limits.

Toxicity

The level of bacterial-derived endotoxin was well within the established limits. It was reduced by the purification process to 25 pg/mg ApoE, according to repeated LAL assays.

B. Comparison of r-ApoE to p-ApoE

1. SDS-PAGE

Figure 4:
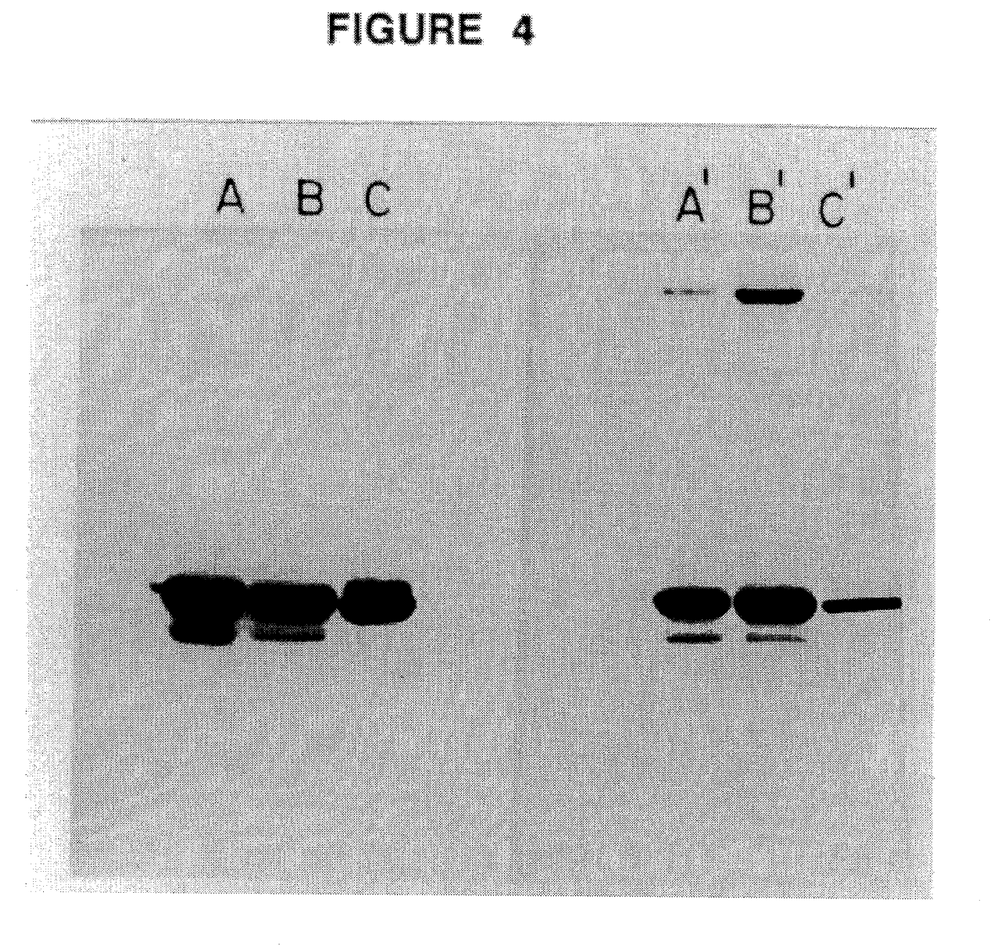

Samples from Batch 01, Batch 02 and p-ApoE were applied on to a 12.5% polyacrylamide-SDS gel in the presence and absence of 2- mercaptoethanol (2 ME) as shown in FIG. 4; see Description of the Figure. The main bands for r-ApoE and p-ApoE migrate identically. The low MW band (32 KD) of r-ApoE represents a cleavage product of the intact protein (34 KD). The upper MW band that appears in the samples applied without 2 ME may represent sulfhydryl bonded oligomer of ApoE.

2. Immune Response on Western Blot

The antigenic identity of r-ApoE can be determined by Western blot. The conditions and sample preparation of the Western blot are similar to those for the SDS-PAGE (FIG. 4). After electrophoresis, the gel is blotted onto nitrocellulose and developed with rabbit polyclonal antiserum specific for human plasmatic ApoE. An additional band, just above the main band, is observed in the plasmatic preparation, but does not appear in the r-ApoE preparations. This higher molecular weight band probably represents a glycosylated form of p-ApoE.

In the r-ApoE preparations, the lower (32 KD) band reacts with antiserum and thus represents a cleavage product of the molecule (see section 5 below). This low MW band also reacts with anti core Apo-E monoclonal antibodies, but does not react with anti N- Terminus monoclonal antibodies.

The high MW bands which appear in all Apo-E preparations on the Western blot that are not treated with 2 ME, may represent multimers.

3. Molecular Weight by Size Exclusion Chromatography

The ApoE MW and aggregation state were determined by fast size exclusion chromatography on SUPEROSE™ 6 column (HR 10/30, Pharmacia). A comparison of SUPEROSE™ 6 elution profiles of r- ApoE and p-ApoE is shown in FIG. 1. The MW of both r-ApoE and p- ApoE were calculated as described in the Description of FIG. 1 to be approximately 65 KD thereby indicating a dimer form.

4. Ultra Violet Absorbance Spectra

Figure 1A:
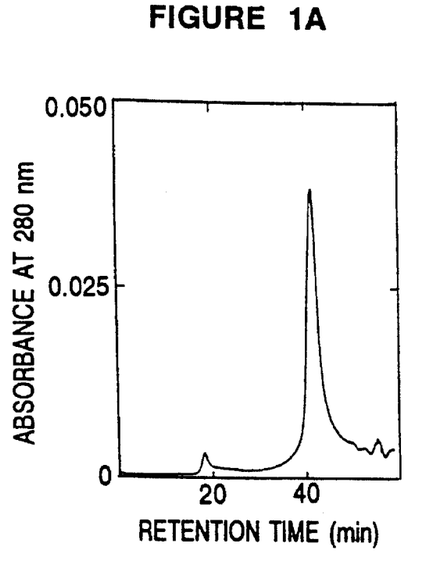
FIGS. 1A–1D: Molecular Weight of Recombinant and Plasmatic ApoE by Size Exclusion Chromatography The ApoE molecular weight, purity, and aggregation state was determined by fast performance size exclusion chromatography on a SUPEROSE™ 6 column (HR 10/30, Pharmacia) (SUPEROSE™ is a trademark for a specific cross-linked agarose matrix). A comparison of profiles of r-ApoE and p-ApoE is shown in this figure.
Figure 1B:
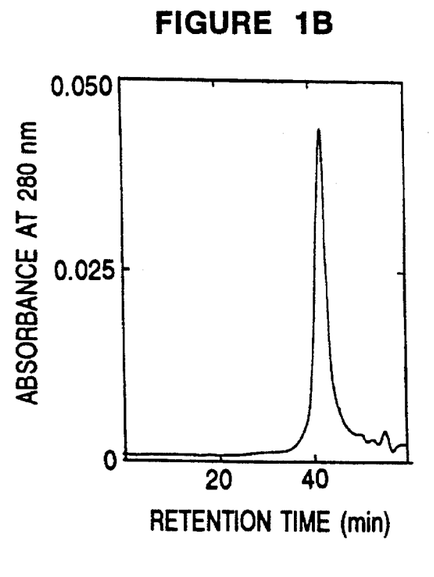
Figure 1C:
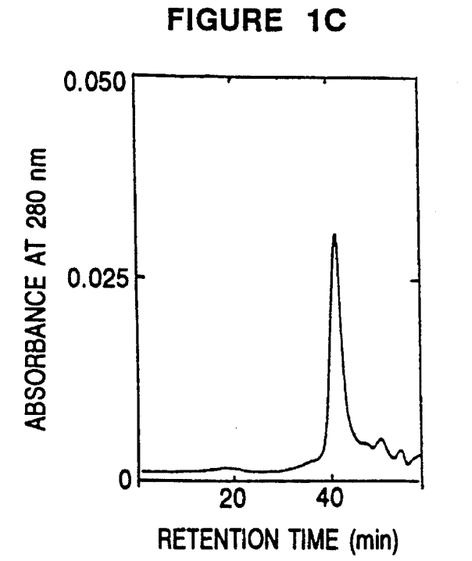
Figure 1D:
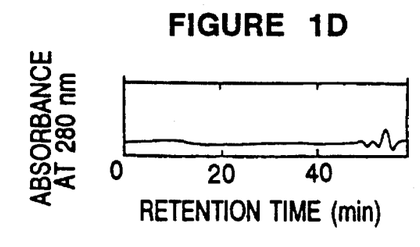
Figure 2A:
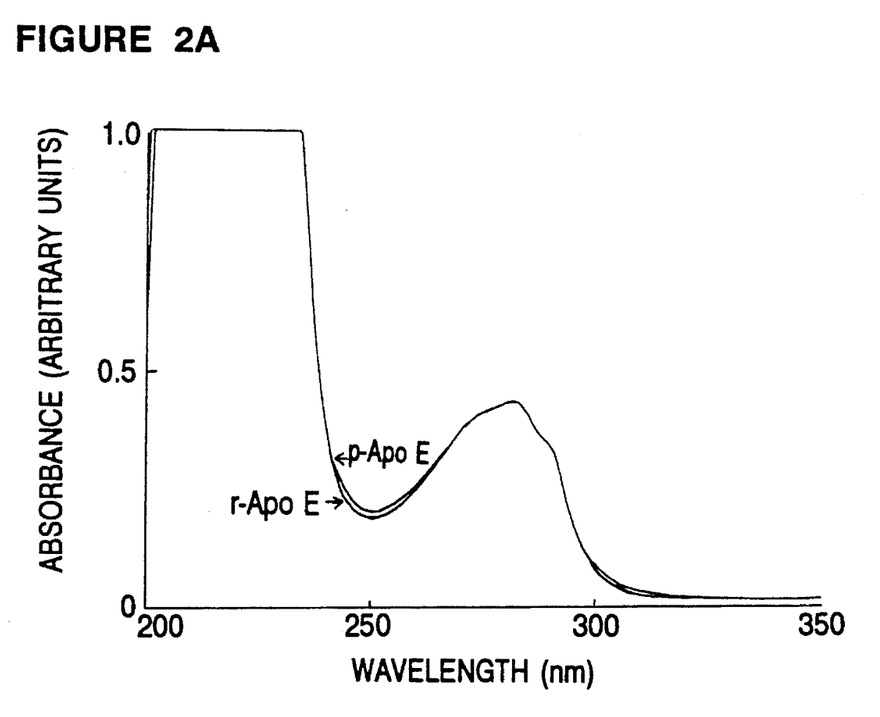
FIGS. 2A–2B: UV Spectra of Recombinant and Plasmatic ApoE
Figure 2B:
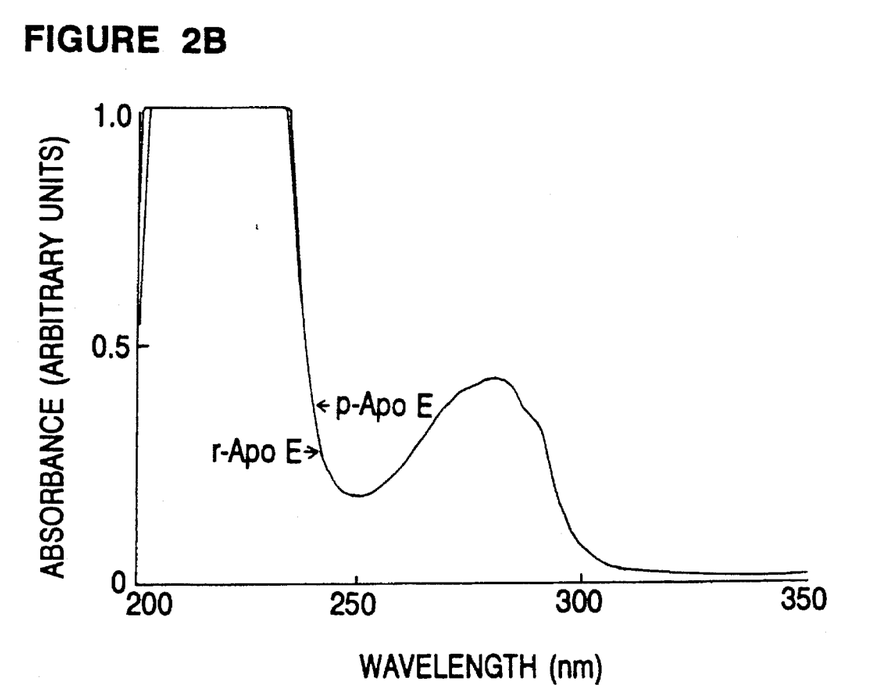

The identity and purity of the r-ApoE and the p-ApoE were also compared by measuring the UV absorbance in the range of 350 to 200 nm, of ApoE batch 01 (FIG. 2A) and batch 02 (FIG. 2B); these spectra are identical to the spectrum of p-ApoE (FIG. 2A and 2B).

5. Amino Acid Analysis

Amino acid composition analysis of the two batches (01 and 02) of r-ApoE analog and p-ApoE were nearly identical; the major difference was that the two samples of r-ApoE analog contained an additional residue of methionine compared to p-ApoE; see Vogel et al., PNAS (USA) 82: 8676–8700 (1985).

N-terminal sequence analysis, 19 cycles, of both batches of r- ApoE analog revealed that the N-sequence corresponds to the first 18 amino acids of authentic p-ApoE with an additional N-terminal methionine: there was no evidence in r-ApoE of a secondary sequence without the additional N-terminal methionine.

The 32 KD band which appears just below the main ApoE band (at 34 KD) has been isolated and its N-terminal sequence analyzed. The result of 14 cycles demonstrated that the N-terminus of this compound corresponds to residues 12 to 25 of p-ApoE and therefore the 32 KD band corresponds to ApoE lacking the first 11 amino acid residues at the N-terminus.

In addition, samples of r-ApoE analog before and after lyophilization were compared in the following tests and shown to behave virtually identical to one another and similar to authentic p-ApoE: SDS-polyacrylamide gel electrophoresis, Western blot analysis, gel filtration and UV spectral analysis.

C. Biological Activity

1. Receptor Binding Assay

Phospholipid complexes of r-ApoE analog and dimyristoylphosphatidylcholine (DMPC) were prepared and isolated as described by T. L. Innerarity et al., *J. Biol. Chem.* 254: 4186–4190 (1979).

Lipoprotein receptor binding assays were performed as described by T. L. Innerarity and R. W. Mahley, *Biochemistry* 17: 1440–1447 (1978). Iodinations of ApoE were performed in 0.10M $NH_4HCO_3$ with Iodo-Beads (Pierce) according to the manufacturer's directions.

Comparison of the receptor binding of ApoE-DMPC complexes demonstrated that the r-ApoE analog possessed binding properties similar to those of the authentic ApoE (p-ApoE). In these experiments, samples of ApoE prepared by Schemes I and II (Examples 3 and 4 respectively) were compared to p-ApoE. Table II shows the results of one set of competition studies using $^{125}$I-LDL bound to ApoB,E receptors (also known as low density lipoprotein-LDL-receptors) on cultured fibroblasts. Tests using ApoE analog after lyophilization demonstrated that lyophilization had no effect on biological activity.

TABLE II

Competition Studies Using $^{125}$I-LDL Bound to ApoB, E Receptors

| ApoE | 50% displacement, µg/ml |
|---|---|
| p-ApoE | 0.050 |
| r-ApoE (Scheme I) | 0.033 |
| r-ApoE (Scheme II) | 0.046 |

2. Lipoprotein Metabolism in Cultured Human Cells

The approach used was to supplement culture systems (human skin fibroblast and Hep G-2 cells) containing $^{125}$I-lipoproteins with exogenous recombinant or plasmatic ApoE (ApoE-3). Without added ApoE, cellular metabolism (binding, cell association and degradation) of VLDL fractions I, II and III was negligible, and of IDL about 50% that of LDL. Exogenous recombinant ApoE analog (before or after lyophilization) caused a many-fold enhancement of VLDL metabolism without any appreciable effect on LDL metabolism.

Conclusion

The improved method of ApoE purification yields a recombinant ApoE analog with properties and characteristics that closely resemble the properties of naturally-occurring ApoE isolated from plasma.

EXAMPLE 6

Pharmaceutical and Diagnostic Uses of ApoE Analog

Examples 3 and 4 describe the purification of a novel ApoE analog which has many potential pharmaceutical, veterinary and diagnostic uses. Some of the uses envisaged for the novel ApoE analog prepared as described in Examples 3 or 4 are described below. The pharmaceutical or veterinary composition containing the ApoE analog should be formulated with a suitable carrier.

1. Prevention add Treatment of Conditions Involving Impaired Lipid and Cholesterol Metabolism We envisage administration of the suitably formulated ApoE analog as purified in Examples 3 and 4 to individuals for therapeutic treatment of atherosclerosis, whether due to dietary or to genetic reasons, by lowering blood cholesterol or lipoprotein levels. We believe the use of ApoE analog may prevent or have therapeutic effect on such conditions as peripheral vascular disease, atherosclerosis, heart attacks and cerebral vascular disease.

Another potential use of ApoE analog is in the treatment of post- myocardial infarction patients. The exogenous administration of the ApoE analog may, in some patients, prevent the re-occlusion of the artery which occurs in approximately 30% of myocardial infarction patients who have been treated by angioplasty or other techniques.

Prophylactic administration of the ApoE analog to prevent atherosclerosis is also considered. This may be especially considered for high risk patients. Example of such patients are those suffering from genetic hyperlipoproteinemia (type III hyperlipoproteinemia) due to the occurrence of abnormal variant forms of ApoE that bind poorly to the lipoprotein (LDL) receptors or to the absence (or almost complete absence) of ApoE.

2. Treatment of Neuronal Injury

We envisage the administration of the suitably formulated ApoE analog as purified in Examples 3 or 4 as the therapeutic agent in treatment of damaged neuronal tissue to promote nerve development and regeneration.

3. Treatment of Tumors Expressing High Levels of LDL Receptors

We envisage using the suitably formulated ApoE analog as purified in Examples 3 or 4 in a pharmaceutical composition for the treatment of tumors which harbor high levels of LDL receptors. The ApoE may contain or be linked physically or chemically to a chemotherapeutic or radiotherapeutic agent to produce a target-orientated therapeutic composition.

4. Diagnosis of LDL Receptor Defects

A lipid emulsion containing the labeled ApoE analog as purified in Examples 3 or 4 may be used to measure the number of ApoB,E (LDL) receptors, and distribution of uptake of labeled ApoE particles. This may possibly be done by scintiscanning techniques, analogous to those used for measurement of thyroid function. These measurements if successful can be used as a diagnostic tool to separate those patients with FH (familial hypercholesterolemia, i.e. having absence of, or abnormalities in, the LDL receptors) from hypercholesterolemia patients who do not have this genetic disease.

5. Diagnosis of Primary and Secondary Sites of Tumor Growth

We envisage using the ApoE analog, the purification of which is described in Examples 3 and 4, as a diagnostic agent of primary and secondary sites of tumor growth. We particularly envisage the use of a lipid emulsion containing labeled ApoE to localize and diagnose tumors harboring high levels of LDL receptors. This may be done by scintiscanning techniques.

6. Immunoregulation

We believe that exogenous administration of the ApoE analog purified as described in Examples 3 or 4 may have therapeutic immunoregulatory activity, and may be used in treatment of autoimmune conditions or diseases involving immunodeficiencies.

7. Lipid Emulsions Containing ApoE as Ligand

Lipid emulsions have high affinity for ApoE. We expect to study the interactions of the ApoE analog with a variety of lipid emulsions and liposome-type particles. This information is to be applied to the fields of drug delivery and specific tissue-targeting of certain lipid moieties such as prostaglandin or leukotriene precursors. Changing the lipid composition of liposomes has been effective in tissue targetting; similarly we envisage alteration in the ApoE content by addition of the ApoE analog purified as described in Examples 3 or 4 to produce similar effects.

EXAMPLE 7

Protection of ApoE From Proteolytic Degradation In Vitro

ApoE, which has a molecular weight of about 35 KD, is susceptible to proteolytic activity both in vivo and in vitro (after bacterial cell disruption). The in vitro cleavage in the presence of bacterial cell extract results in the formation of two polypeptides with approximate molecular weights of 14 KD and 21 KD.

We surprisingly found that the in Vitro proteolytic degradation of ApoE was reduced dramatically when chemicals such as short chain fatty acids were added to an assay mix containing purified r-ApoE. EDTA also reduced the proteolytic activity.

The in vitro protease activity of the bacterial cell free extract on ApoE was measured using the following 500 ml assay mix which contains:

100 μl purified ApoE (25 μg).

10–50 μl of bacterial cell-free extract.

50 μl chemical such as butyric acid or beta-hydroxybutyrate or hexanoic acid (all neutralized) or protease inhibitor such as trasylol (aprotinin) or EDTA.

300 μl 0.1M tris/acetate buffer pH=6.7.

The bacterial cell-free extract was prepared from cultures of host E. coli cells containing no plasmid, grown at 30° C. and heat-shocked for 2 hours at 42° C. 10 $OD_{660}$ equivalents of cells were sonicated in 2 ml of 0.1M tris/acetate buffer, pH=6.7.

The reaction mixture was incubated at 42° C. for 90 minutes after which 20 μl of mixture was removed, brought to 100 μl with 0.1M tris/HCl buffer pH=8.0, and 50 μl of 3×SDS gel sample buffer was added. (3×SDS gel sample buffer contains 187.5 mM tris/HCl pH=6.8, 2.1M beta-mercaptoethanol, 9% SDS, 30% w/v glycerol and 0.5% bromophenol blue). 20 μl of the resulting mixture was added to slots of 12.5% polyacrylamide gels following 10 minutes of heat treatment at 100° C.

Following electrophoresis, the gels were stained with Coomassie blue reagent. The intensity of the visualized bands was estimated by a scanner.

The ApoE (34 KD) band intensities on SDS gels of samples containing no bacterial extract or chemical were used as the controls and compared to those of treated samples. The 14 KD and 21 KD bands produced as a result of proteolytic digestion both reacted with anti-ApoE antibody. However, these 14 KD and 21 KD bands were not generated in the presence of effective amounts of the above-listed chemicals.

Table III summarizes the effect of a variety of chemicals on the proteolytic activity of bacterial cell-free extract on ApoE. This table clearly demonstrates that fatty acids and also EDTA prevent the degradation of ApoE by bacterial extract. Hexanoic (caproic) acid, EDTA, butyric acid and beta-hydroxybutyrate (all acids neutralized) are all preferred inhibitors of this proteolytic activity, in order of increasing inhibitory activity.

It is envisaged that other fatty acids, fatty acid precursors, triglycerides and triglyceride precursors could also be used to inhibit ApoE degradation.

It was decided, for reasons of cost and convenience, to choose beta-hydroxybutyrate (sodium salt) as the protease inhibitor at the time of cell disruption (Examples 3A and 4A). EDTA was also added in the alternative method, Scheme II (Example 4A). The preferred concentration of the above inhibitors of protease degradation at the time of cell disruption is about 0.1%–1.0% with the most preferred concentration being about 0.2%.

TABLE III

EFFECT OF VARIOUS CHEMICALS ON IN VITRO DEGRADATION OF PURIFIED APOE BY BACTERIAL EXTRACT

| Chemical Added | Bacterial Extract Added | Intact ApoE (34 KD band) Remaining[1] |
|---|---|---|
| None | Yes | + |
| None (control) | No | ++++ |
| EDTA | Yes | +++ |
| Butyric acid | Yes | +++ |

TABLE III-continued

EFFECT OF VARIOUS
CHEMICALS ON IN VITRO DEGRADATION
OF PURIFIED APOE BY BACTERIAL EXTRACT

| Chemical Added | Bacterial Extract Added | Intact ApoE (34 KD band) Remaining[1] |
|---|---|---|
| Beta-hydroxybutyric | Yes | ++ |
| Hexanoic acid | Yes | +++(+) |
| Trasylol | Yes | + |

1.
++++ = about 100% of control.
+++ = about 75% of control.
++ = about 50% of control.
+ = about 25% of control.

What is claimed is:

1. A method for increasing the production of recombinant ApoE or polypeptide analog thereof in an *E. coli* host cell by adding to a medium in which the host is growing an effective amount of a compound selected from the group consisting of the neutralized fatty acids sodium propionate, n-butyric acid (neutralized) and beta-hydroxybutyric acid (neutralized), or selected from the group consisting of the triglycerides triacetin, tributyrin, and tricaprylin, or selected from the group consisting of the triglyceride precursors 1-monomyristoyl-rac-glycerol, 1-monopalmitoyl-rac-glycerol, DL-α-hydroxyvaleric acid and glycerol or acetate and subsequently purifying the recombinant ApoE to obtain soluble recombinant ApoE by a method which comprises:

(a) treating the *E. coli* cells in the presence of magnesium ions so as to obtain a lysate containing insoluble recombinant ApoE or polypeptide analog thereof;

(b) recovering from the lysate insoluble material including insoluble recombinant ApoE or polypeptide analog thereof;

(c) treating the insoluble material so recovered with a solution containing a non-ionic detergent to obtain solubilized recombinant ApoE or polypeptide analog thereof;

(d) treating the solubilized recombinant ApoE or polypeptide analog thereof so as to concentrate and purify the recombinant ApoE or polypeptide analog thereof; and (e) recovering the resultant concentrated purified recombinant ApoE or polypeptide analog thereof.

2. The method of claim 1, wherein the acetate is sodium acetate.

3. The method of claim 2 wherein the effective amount of sodium acetate produces a medium concentration of 0.1% to 1% sodium acetate.

4. The method of claim 3 wherein the medium concentration of sodium acetate is about 0.5%.

5. A method of claim 1, wherein the effective amount of the fatty acid, the triglyceride or the triglyceride precursor produces a final concentration in the culture of about 0.1% to 0.5%.

6. A method of claim 5 wherein the final concentration in the culture is about 0.2%.

* * * * *